(12) United States Patent
Liu et al.

(10) Patent No.: US 11,225,491 B2
(45) Date of Patent: Jan. 18, 2022

(54) THIAZOLO-PYRIMIDINE HIV-1 REVERSE TRANSCRIPTASE INHIBITOR, PREPARATION METHOD THEREFOR, AND USES THEREOF

(71) Applicant: SHAN DONG UNIVERSITY, Jinan (CN)

(72) Inventors: Xinyong Liu, Jinan (CN); Dongwei Kang, Jinan (CN); Peng Zhan, Jinan (CN); Zhao Wang, Jinan (CN); Gaoshan Wu, Jinan (CN)

(73) Assignee: SHAN DONG UNIVERSITY, Jinan (CN)

( * ) Notice: Subject to any disclaimer, the term of this patent is extended or adjusted under 35 U.S.C. 154(b) by 30 days.

(21) Appl. No.: 16/765,076

(22) PCT Filed: Oct. 12, 2018

(86) PCT No.: PCT/CN2018/110112
§ 371 (c)(1),
(2) Date: May 18, 2020

(87) PCT Pub. No.: WO2019/196369
PCT Pub. Date: Oct. 17, 2019

(65) Prior Publication Data
US 2020/0361959 A1    Nov. 19, 2020

(30) Foreign Application Priority Data

Apr. 12, 2018 (CN) .......................... 201810336409.9

(51) Int. Cl.
*C07D 513/04* (2006.01)
*A61P 31/18* (2006.01)

(52) U.S. Cl.
CPC ............ *C07D 513/04* (2013.01); *A61P 31/18* (2018.01)

(58) Field of Classification Search
CPC .............................. C07D 513/04; A61P 31/18
USPC ...................................................... 514/260.1
See application file for complete search history.

(56) References Cited

FOREIGN PATENT DOCUMENTS

WO    WO-2016197589 A1 * 12/2016 ........... C07D 495/04

* cited by examiner

*Primary Examiner* — Kahsay Habte
(74) *Attorney, Agent, or Firm* — CBM Patent Consulting, LLC

(57) ABSTRACT

The present invention belongs to the field of pharmaceutical technology, specifically disclosing thiazolopyrimidine compounds with the general formulas I and II. Also including theirs polycrystalline and eutectic, prodrugs and derivatives with same biologically functional, methods for their preparation, and compositions containing one or more of these compounds in the drugs application of treatment and prevention of human immunodeficiency virus.

4 Claims, No Drawings

THIAZOLO-PYRIMIDINE HIV-1 REVERSE TRANSCRIPTASE INHIBITOR, PREPARATION METHOD THEREFOR, AND USES THEREOF

FIELD OF THE INVENTION

The present invention relates to thiazolopyrimidine derivatives, pharmaceutically acceptable additional salts or prodrugs having HIV replication inhibiting properties. Also described herein are the preparation of these derivatives and pharmaceutical compositions comprising them.

BACKGROUND OF THE INVENTION

Human immunodeficiency virus type 1 (HIV-1) is the mainly causative agent of acquired immune deficiency syndrome (AIDS), which is one of the major diseases that seriously endanger human health. In the life cycle of HIV-1, reverse transcriptase (RT) is responsible for reverse transcription of single-stranded RNA carrying viral genetic information into double-stranded DNA, and is the crucial target of anti-AIDS drug design. HIV-1 non-nucleoside reverse transcriptase inhibitors (NNRTIs) is an important part of highly active antiretroviral therapy (HAART) for their advantages of high efficiency and specificity. Although the implementation of HAART significantly prolongs the survival time of patients, the problems of drug resistance and side effects caused by long-term use have forced researchers to seek new and effective HIV-1 inhibitors.

Diarylpyrimidine (DAPY) is a typical type of HIV-1 NNRTIs and has promising anti-resistance profiles, both the second-generation HIV-1 NNRTIs Etravirine (ETR) and Rilpivirne (RPV) are belongs to DAPY derivatives. However, these compounds contain too much aromatic ring structure, resulting in their low water solubility and oral bioavailability. In addition, they also suffered from serious side effects and cross-resistance in clinical use. For example, ETR should be administered multiple times a day and is accompanied by severe skin allergic reactions. RPV can cause toxic and side effects, such as depression, acute respiratory distress syndrome, headache and rash. Therefore, the research and development of a new generation of highly effective anti-drug NNRTIs is a major scientific task of current anti-AIDS drug research.

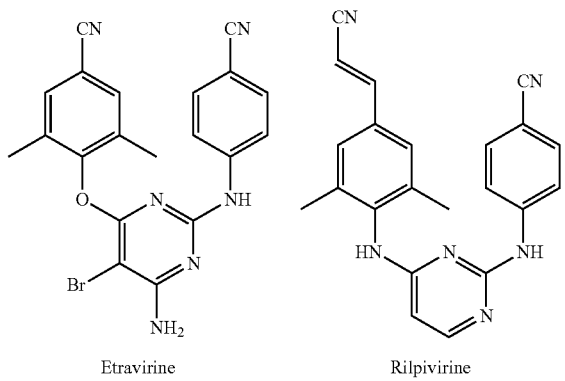 [SMILES: Cc1cc(C#N)cc(C)c1Oc1nc(Nc2ccc(C#N)cc2)nc(N)c1Br ; Cc1cc(/C=C/C#N)cc(C)c1Nc1ccnc(Nc2ccc(C#N)cc2)n1]

Etravirine          Rilpivirine

SUMMARY OF THE INVENTION

In view of the deficiencies of the prior art, the present invention provides a series of thiazolopyrimidine derivatives and their preparation method, as well as their applications as HIV-1 inhibitors.

1. Thiazolopyrimidine Derivatives

The invention provides a series of thiazolopyrimidine compounds of formula I and formula II, and pharmaceutically acceptable additional salt or prodrugs.

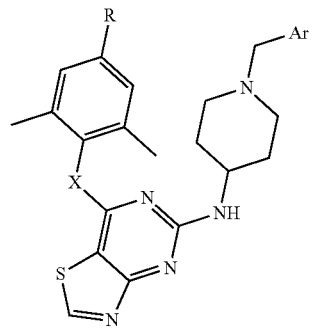

I

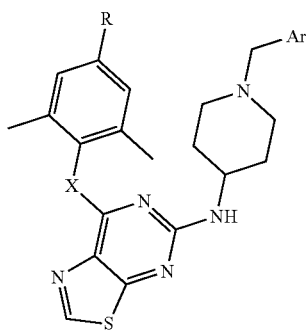

II

Wherein

X is O or NH;

R is $CH_3$, CN or CH=CHCN;

Ar is phenyl or pyridyl; or $SO_2NH_2$, $SO_2NH_2CH_3$, $SO_2NH(CH_2)_3$, $SO_2NH(CH_2)_2O$, $SO_2CH_3$, $CONH_2$, halogen, $NO_2$, CN, $NH_2$, $CF_3$, $NHCH_3$, OH, COOH, $CH_2OH$, $CO_2Me$, $OCH_3$, and $NHCOCH_3$ substituted phenyl; substituents are ortho, meta and para single or multiple substitutions.

more preferably, thiazolopyrimidine derivatives are compounds as follow:

| Code | Structure |
|---|---|
| SZ1 | 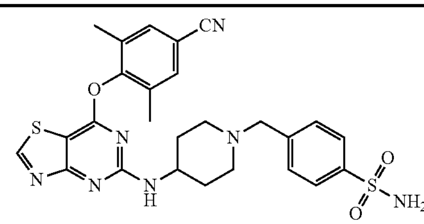 |
| SZ2 | 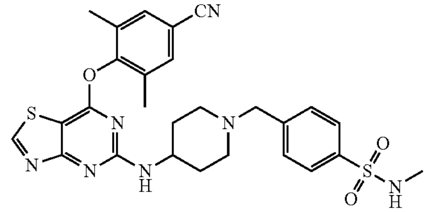 [SMILES: CNS(=O)(=O)c1ccc(CN2CCC(Nc3nc(Oc4c(C)cc(C#N)cc4C)c4scnc4n3)CC2)cc1] |

| Code | Structure |
|---|---|
| SZ3 | |
| SZ4 | |
| SZ5 | |
| SZ6 | |
| SZ7 | |
| SZ8 | |
| SZ9 | 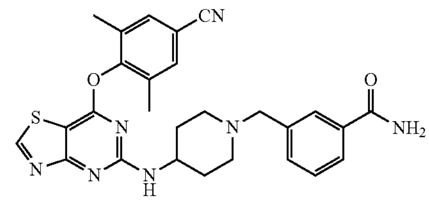 [SMILES: Cc1cc(C#N)cc(C)c1Oc1nc(NC2CCN(Cc3cccc(C(N)=O)c3)CC2)nc2ncsc12] |
| SZ10 | 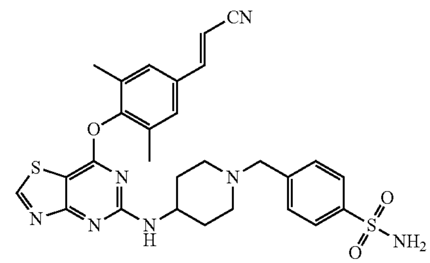 [SMILES: Cc1cc(/C=C/C#N)cc(C)c1Oc1nc(NC2CCN(Cc3ccc(S(N)(=O)=O)cc3)CC2)nc2ncsc12] |
| TZ1 | 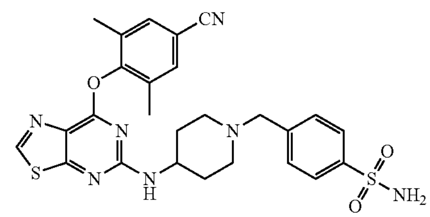 [SMILES: Cc1cc(C#N)cc(C)c1Oc1nc(NC2CCN(Cc3ccc(S(N)(=O)=O)cc3)CC2)nc2scnc12] |
| TZ2 | 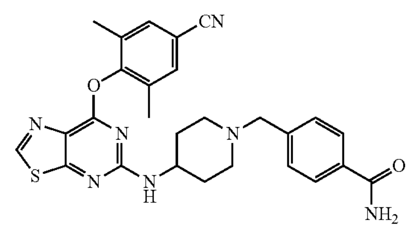 [SMILES: Cc1cc(C#N)cc(C)c1Oc1nc(NC2CCN(Cc3ccc(C(N)=O)cc3)CC2)nc2scnc12] |
| TZ3 | 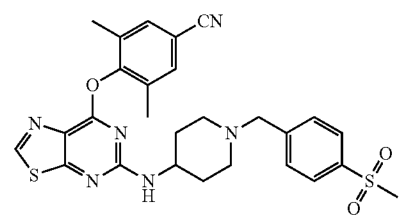 [SMILES: Cc1cc(C#N)cc(C)c1Oc1nc(NC2CCN(Cc3ccc(S(C)(=O)=O)cc3)CC2)nc2scnc12] |
| TZ4 | 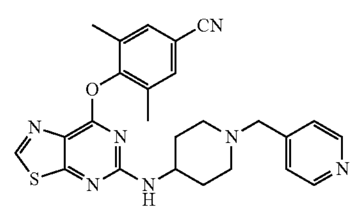 [SMILES: Cc1cc(C#N)cc(C)c1Oc1nc(NC2CCN(Cc3ccncc3)CC2)nc2scnc12] |
| TZ5 | 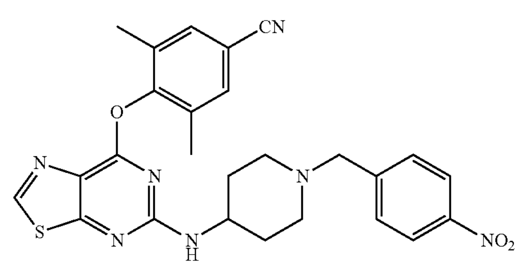 [SMILES: Cc1cc(C#N)cc(C)c1Oc1nc(NC2CCN(Cc3ccc([N+](=O)[O-])cc3)CC2)nc2scnc12] |

| Code | Structure |
|---|---|
| TZ6 | 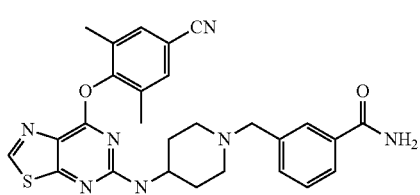 |
| TZ7 | 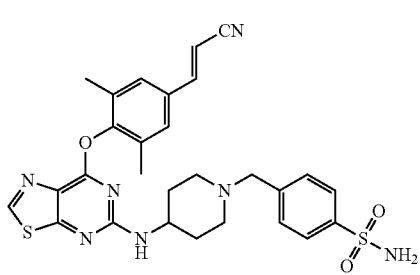 [SMILES: Cc1cc(/C=C/C#N)cc(C)c1Oc1nc(NC2CCN(Cc3ccc(S(N)(=O)=O)cc3)CC2)nc2scnc12] |
| TZ8 | 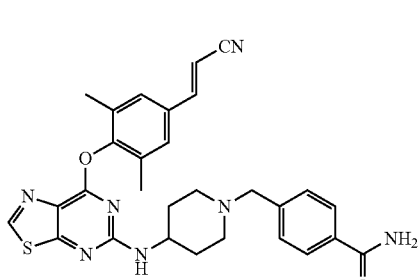 |

The term "pharmaceutically acceptable salt" as used in the present invention means that the salt of the compound is suitable for contact with the tissue of a human or lower animal without any inappropriate toxicity, irritation and allergy within a reliable medical evaluation range reaction, with a reasonably reasonable ratio of profit to risk. They are usually water or oil soluble or dispersible, and can be effectively used for its intended use. It includes pharmaceutically acceptable acid addition salts and base addition salts, which can be effectively used as specific purpose and compatible with compounds described here. The pharmaceutical acceptable salts are reviewed in S. M. Birge et al. J. Pharm. Sci., 1977, 66, 1-19.

2. Preparation of Thiazolopyrimidin Derivatives

The preparation method of thiazolopyrimidin derivatives is as follows: The starting material 2,4-dichloro-substituted thiazolopyrimidin 1a or 1b were first reacted with substituted phenol or aniline gave intermediates 2a or 2b via nucleophilic substitution reaction. Then treatment of 2a or 2b with N-Boc-4-aminopiperidine afforded the key intermediates 3a or 3b, which were directly deprotected with trifluoroacetic acid in dichloromethane to afford the corresponding analogues 4a or 4b. Finally, intermediates 4a or 4b were converted into target compounds by nucleophilic substitution with various substitutes of benzyl chloride or benzyl bromide. The synthetic routes are as follows:

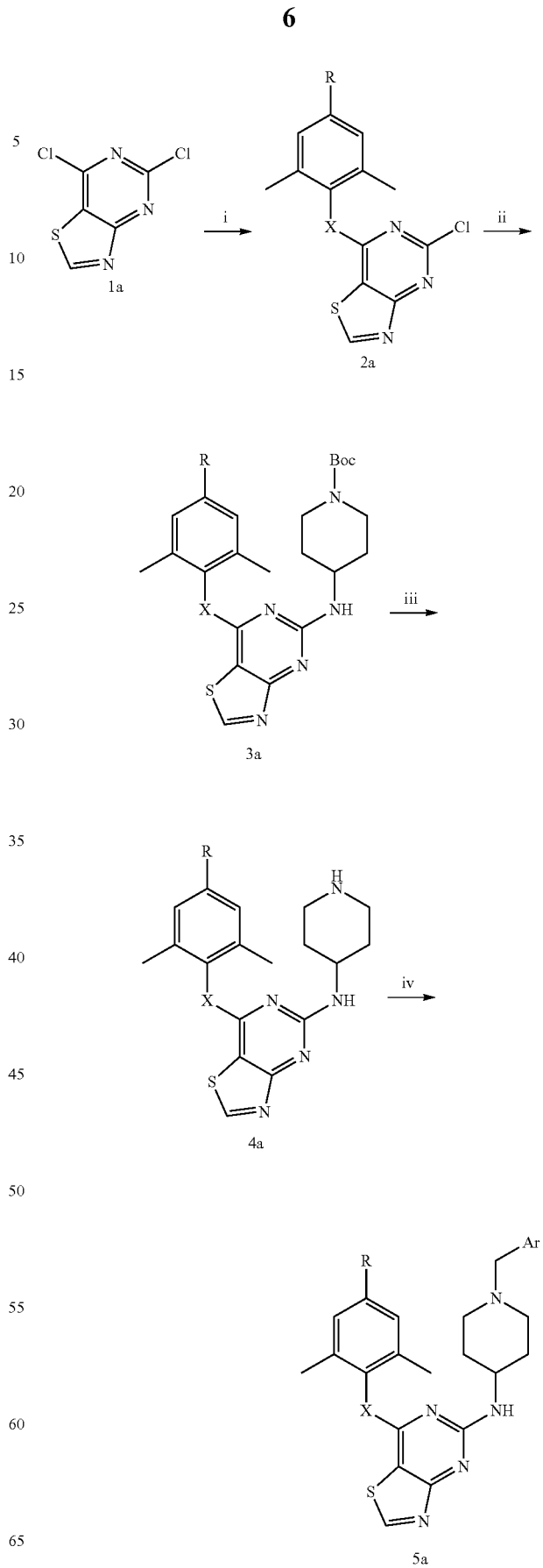

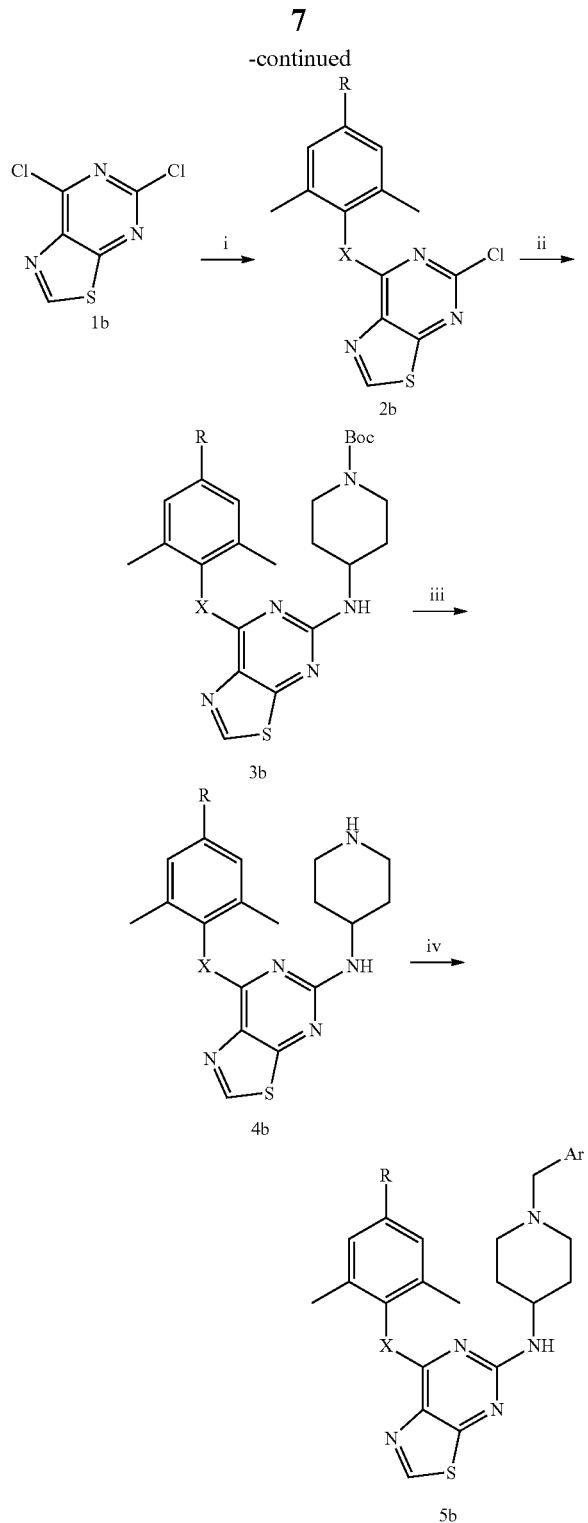

Reagents and conditions: (i) substituted phenol or aniline, DMF, K$_2$CO$_3$, r.t.; (ii) N-Boc-4-aminopiperidine, DMF, K$_2$CO$_3$, 120° C.; (iii) TFA, DCM, r.t.; (iv) substituted benzyl bromine, DMF, K$_2$CO$_3$, r.t.

Wherein, X, R, Ar are the same as general formula I or II.

Wherein, substituted phenol or aniline is selected from 2,4,6-trimethylphenol, 2, 6-dimethyl-4-cyanophenol, 2,6-dimethyl-4-(E)-cyanovinylphenol, 2,4,6-trimethylaniline, 2, 6-dimethyl-4-cyanoaniline, and 2,6-dimethyl-4-(E)-cyanovinylanilinen.

Wherein, the substituted benzyl chloride/bromide is selected from 1-chloro-2-(chloromethyl)benzene, 1-chloro-3-(chloromethyl)benzene, 1-chloro-4-(chloromethyl) benzene, 1-bromo-2-(bromomethyl)benzene, 1-bromo-3-(bromomethyl)benzene, 1-bromo-4-(bromomethyl)benzene, 1-(chloromethyl)-2-fluorobenzene, 1-(chloromethyl)-3-fluorobenzene, 1-(chloromethyl)-4-fluorobenzene, 1-(bromomethyl)-2,4-difluorobenzene, 1-(bromomethyl)-3,4-difluorobenzene, 2-(chloromethyl)benzonitrile, 3-(chloromethyl)benzonitrile, 4-(chloromethyl)benzonitrile, 1-(cholomethyl)-2-nitrobenzene, 1-(chloromethyl)-3-nitrobenzene, 1-(chloromethyl)-4-nitrobenzene, 1-(chloromethyl)-2-methoxybenzene, 1-(chloromethyl)-3-methoxybenzene, 1-(chloromethyl)-4-methoxybenzene, 1-(bromomethyl)-4-(methylsulfonyl) benzene, 4-(bromomethyl)benzenesulfonamide, 3-(bromomethyl)benzenesulfonamide, 2-(bromomethyl)benzamide, N-(4-(bromomethyl)phenyl)formamide, ethyl 4-(bromomethyl) benzoate, 4-(bromomethyl)benzamide, 3-(bromomethyl)benzamide, N-(4-(bromomethyl)phenyl) methanesulfonamide, etc.

The room temperature of the present invention is from 20 to 30° C.

3. Activity Against Wide-Type and Mutant HIV-1 Strains and Use Thereof

Antiviral potency was evaluated in MT-4 cell cultures infected with WT HIV-1 strain (IIIB) as well as cells infected with a panel of NNRTI-resistant single- and double-mutant strains, such as K103N, Y181C, Y188L, F227L/V106A and K103N+Y181C (RES056). Nevirapine (NVP) and etravirine (ETR) were selected as control drugs. The values of EC$_{50}$ (anti-HIV potency) and CC$_{50}$ (cytotoxicity) of the synthesized compounds are summarized in Tables 1-2.

The results demonstrated that most of the synthesized thiazolopyrimidin compounds exhibited more potent activity than the approved drug ETR, displaying nanomolar EC$_{50}$ values towards a panel of wild-type (WT), single-mutant and double-mutant HIV-1 strain. Compound SZ1, SZ2, SZ6, SZ7, TZ1-4 were the most potent inhibitors. Moreover, they were demonstrated with lower cytotoxicity and a huge selectivity index (SI) value (ratio of CC$_{50}$/EC$_{50}$) of >100,000 compared to the listed drugs. Overall, the results indicate that thiazolopyrimidin compounds hold great promise as potential next-generation anti-HIV drug candidates with significantly improved activity, high selectivity, and outstanding drug resistance profiles, and they have great value for further research and development.

Also described here are thiazolopyrimidin derivatives used as HIV-1 NNRTIs, furthermore, these HIV-1 inhibitors will be used as anti-AIDS drugs.

Also described here are pharmaceutical composition comprising thiazolopyrimidin derivatives, and with one or more kind of pharmaceutically acceptable carrier or excipient.

The present invention provides novel thiazolopyrimidin derivatives, their preparation method, anti-HIV-1 activity screening results and their first application in anti-HIV-1 field. The thienopyrimidine derivatives of the present invention have been proved to be useful as HIV-1 inhibitors and have high application value. In particular, the inhibitors could be used as anti-AIDS drugs.

EXAMPLES

Selected examples are listed as follows, the invention includes these compounds disclosed herein but not confined to them.

The synthetic routes involved in the examples are as follows:
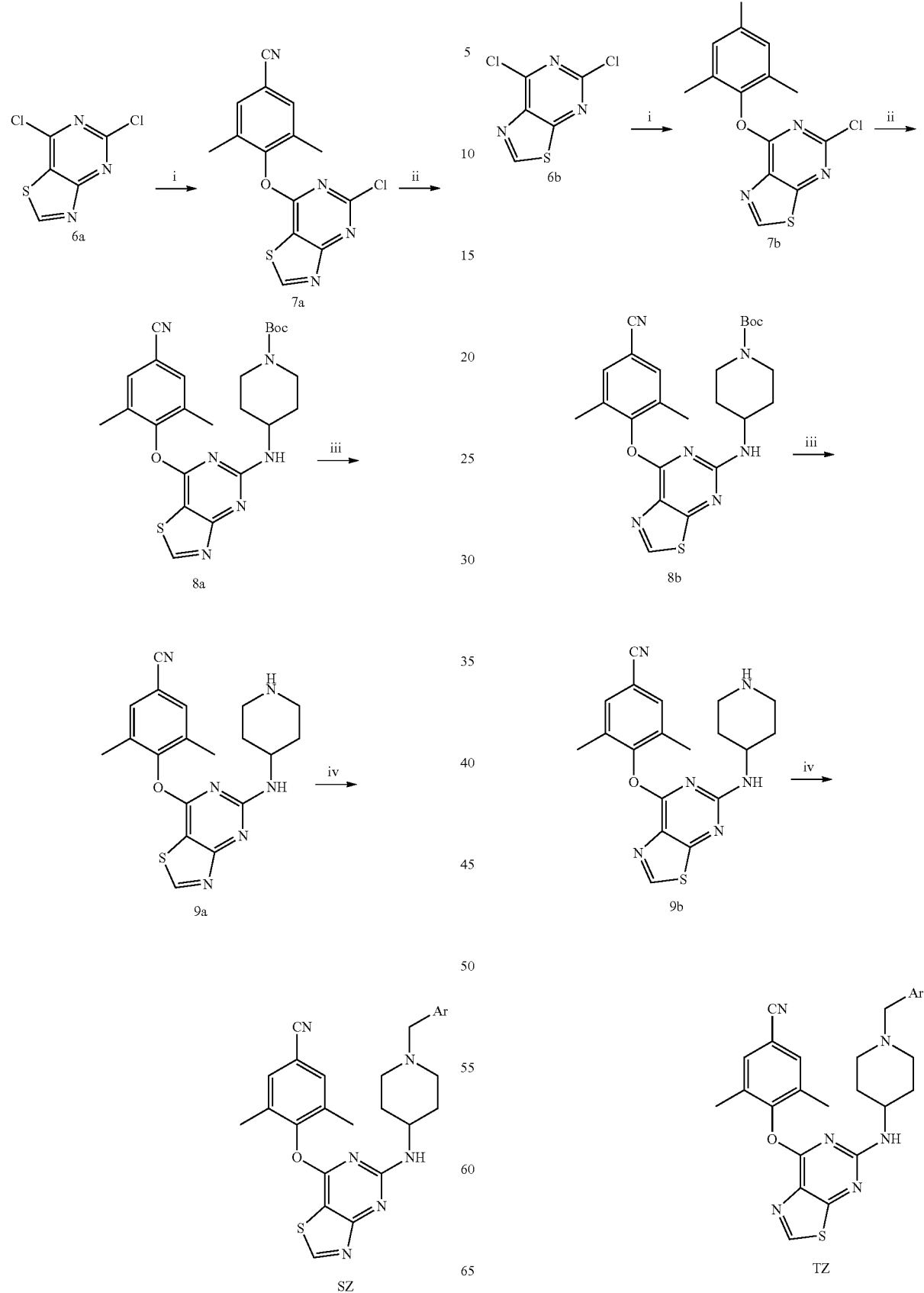

Example 1: 4-((5-chlorothiazolo[4,5-d]pyrimidin-7-yl)oxy)-3,5-dimethylbenzonitrile (7a)

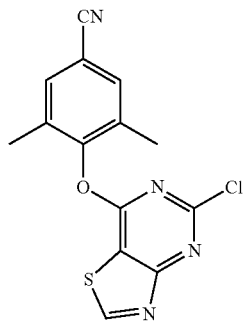

7a

A reaction mixture of 4-hydroxy-3,5-dimethylbenzonitrile (1.5 g, 10 mmol) and potassium carbonate (1.7 g, 12 mmol) in 30 mL of DMF was stirred at 25° C. for 15 min, and then 5,7-dichlorothiazolo[4,5-d]pyrimidine (2.1 g, 10 mmol) was added to it. Stirring was continued for an additional 2.0 h (monitored by TLC), then the mixture was poured into ice water, the precipitated white solid was collected by filtration, washed with cold water, and recrystallized in DMF-H$_2$O to provide the desired product 7a as white solid with 94% yield, mp: 250-253° C. $^1$H NMR (400 MHz, DMSO-d$_6$) δ 9.60 (s, 1H), 7.78 (s, 2H), 2.14 (s, 6H). HRMS: m/z 317.0255 [M+1]$^+$. C$_{14}$H$_9$ClN$_4$OS (316.0186).

Example 2: 3,5-dimethyl-4-((5-(piperidin-4-ylamino)thiazolo[4,5-d]pyrimidin-7-yl)oxy) benzonitrile (9a)

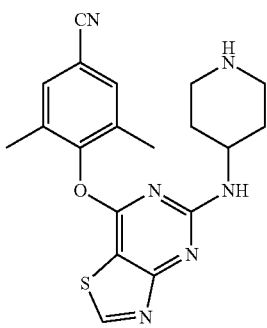

9a

A solution of 7a (1.0 g, 3.17 mmol), tert-butyl 4-aminopiperidine-1-carboxylate (0.83 g, 3.80 mmol), and anhydrous K$_2$CO$_3$ (0.87 g, 6.33 mmol) in 5 mL of DMF was heated at 120° C. for 10 h. After completion (monitored by TLC), the mixture was cooled to room temperature and 50 mL of ice water was added. The reaction mixture was continuously stirred for another 30 min and the resulting precipitate was collected and dried to give the intermediate 8a, which was used directly without purification. To a solution of 8a (1.26 g, 2.53 mmol) in dichloromethane (DCM) (4 mL) was added trifluoroacetic acid (TFA) (2.22 mL, 30 mmol) at room temperature. After the mixture was stirred for 4 h (monitored by TLC), it was alkalized to pH 9 with saturated sodium bicarbonate solution and washed with saturated salt water (15 mL). The aqueous phase was extracted with DCM (3×5 mL). The combined organic phase was dried over Na$_2$SO$_4$. The filtrate was concentrated and purified by column chromatography on silica gel to get 9a as a white solid with 64% yield, mp: 130-132° C. $^1$H NMR (400 MHz, DMSO-d$_6$) δ 9.12 (s, 1H, thiazole-H), 8.50 (d, J=5.9 Hz, 1H, NH), 7.67 (s, 2H, C$_3$, C$_5$-Ph-H), 3.65-3.62 (m, 1H), 2.78-2.76 (m, 2H), 2.10 (s, 6H), 1.86-1.75 (m, 2H), 1.72-1.55 (m, 4H). HRMS: m/z 381.1489 [M+1]$^+$. C$_{19}$H$_{20}$N$_6$OS (380.1419).

Example 3: 4-((5-chlorothiazolo[5,4-d]pyrimidin-7-yl)oxy)-3,5-dimethylbenzonitrile (7b)

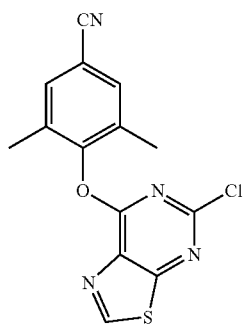

7b

The synthetic method was similar to that described for 7a, with the difference that the starting material was 5,7-dichlorothiazolo[5,4-d]pyrimidine. White solid, 93% yield, mp: 265-268° C. $^1$H NMR (400 MHz, DMSO-d$_6$) δ 9.06 (s, 1H), 7.67 (s, 2H, C$_3$, C$_5$-Ph-H), 2.14 (s, 6H). ESI-MS: m/z 317.0260 [M+1]$^+$. C$_{14}$H$_9$ClN$_4$OS (316.0186).

Example 4: 3,5-dimethyl-4-((5-(piperidin-4-ylamino)thiazolo[4,5-d]pyrimidin-7-yl)oxy) benzonitrile (9b)

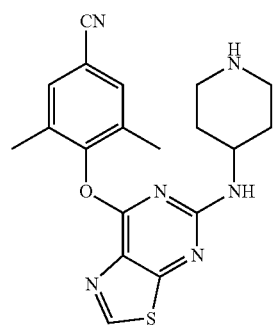

9b

The synthetic method was similar to that described for 9a, with the difference that the starting material was 4-((5-chlorothiazolo[5,4-d]pyrimidin-7-yl)oxy)-3,5-dimethylbenzonitrile (7b). White solid, 90% yield, mp: 135-138° C. $^1$H NMR (400 MHz, DMSO-d$_6$) δ 9.06 (s, 1H, thiazole-H), 8.42 (d, J=7.2 Hz, 1H, NH), 7.67 (s, 2H, C$_3$, C$_5$-Ph-H), 3.65-3.63 (m, 1H), 2.79-2.78 (m, 2H), 2.10 (s, 6H), 1.86-1.82 (m, 2H), 1.70-1.52 (m, 4H). HRMS: m/z 381.1492 [M+1]$^+$. C$_{19}$H$_{20}$N$_6$OS (380.1419).

Example 5: Preparation of SZ1-9 and TZ1-5

Compounds 9a or 9b (0.5 mmol) was dissolved in anhydrous DMF (5 mL) in the presence of anhydrous $K_2CO_3$ (0.14 g, 1.0 mmol), followed by addition of appropriate substituted benzyl chloride (bromine) (0.6 mmol). The reaction mixture was stirred at room temperature for 4-12 h. The solvent was removed under reduced pressure, and then water (20 mL) was added. Extracted with ethyl acetate (3×10 mL), and the organic phase was washed with saturated sodium chloride (10 mL), then dried over anhydrous $Na_2SO_4$ to give the corresponding crude product, which was purified by flash column chromatography and recrystallized from Ethyl acetate (EA)/petroleum ether (PE) to afford the target compounds SZ1-9 and TZ1-5.

4-((4-(7-(4-cyano-2,6-dimethylphenoxy)thiazolo[4,5-d]pyrimidin-5-yl)amino)piperidin-1-yl)methyl)benzenesulfonamide (SZ1)

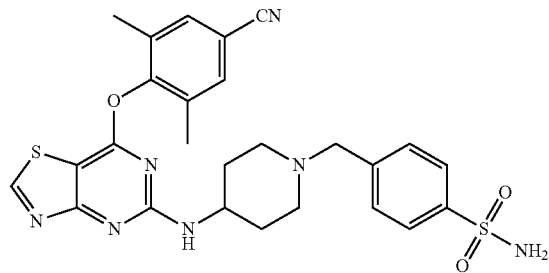 [SMILES: Cc1cc(C#N)cc(C)c1Oc1nc(NC2CCN(Cc3ccc(S(N)(=O)=O)cc3)CC2)nc2ncsc12]

Starting with 9a and 4-(bromomethyl)benzenesulfonamide to afford SZ1 as a white solid. Yield: 78%, mp: 139-142° C.

$^1$H NMR (400 MHz, DMSO-$d_6$) δ 9.06 (s, 1H, thiazole-H), 8.43 (d, J=7.5 Hz, 1H, NH), 7.79 (d, J=7.8 Hz, 2H, $C_3$, $C_5$-Ph'-H), 7.67 (s, 2H, $C_3$, $C_5$-Ph'-H), 7.47 (d, J=8.0 Hz, 2H, $C_2$, $C_6$-Ph'-H), 7.32 (s, 2H, $SO_2NH_2$), 3.67-3.64 (m, 1H), 3.50 (s, 2H, N—$CH_2$), 2.81-2.67 (m, 2H), 2.09 (s, 6H), 1.88-1.75 (m, 2H), 1.65-1.39 (s, 4H). $^{13}$C NMR (100 MHz, DMSO-$d_6$) δ 156.7, 154.5, 150.0, 143.3, 143.6, 132.9, 132.7, 129.0, 126.1, 119.3, 108.9, 61.9, 52.1, 48.4, 39.4, 31.5, 16.2. HRMS: m/z 550.1692 [M+1]$^+$. $C_{26}H_{27}N_2O_3S_2$ (549.1617).

4-((4-(7-(4-cyano-2,6-dimethylphenoxy)thiazolo[4,5-d]pyrimidin-5-yl)amino)piperidin-1-yl)methyl)-N-methylbenzenesulfonamide (SZ2)

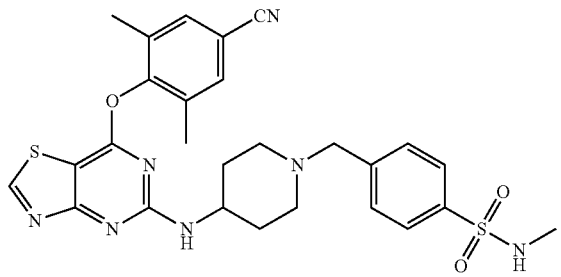 [SMILES: CNS(=O)(=O)c1ccc(CN2CCC(Nc3nc(Oc4c(C)cc(C#N)cc4C)c4scnc4n3)CC2)cc1]

Starting with 9a and 4-(bromomethyl)-N-methylbenzenesulfonamide to afford SZ2 as a white solid. Yield: 58%, mp: 120-123° C.

$^1$H NMR (400 MHz, DMSO-$d_6$) δ 9.06 (s, 1H, thiazole-H), 8.95 (s, 1H, $SO_2NH$), 8.44 (d, J=7.4 Hz, 1H, NH), 7.73 (d, J=7.7 Hz, 2H, $C_3$, $C_5$-Ph'-H), 7.67 (s, 2H, $C_3$, $C_5$-Ph'-H), 7.53 (d, J=8.3 Hz, 2H, $C_2$, $C_6$-Ph'-H), 3.67-3.64 (m, 1H), 3.52 (s, 2H, N—$CH_2$), 3.34 (s, 3H), 2.80-2.78 (m, 2H), 2.10 (s, 6H), 1.87 (t, J=11.6 Hz, 2H), 1.74-1.47 (m, 4H). $^{13}$C NMR (100 MHz, DMSO-$d_6$) δ 161.1, 156.6, 154.5, 150.2, 144.0, 138.2, 133.0, 132.7, 129.7, 129.1, 128.2, 127.4, 127.2, 127.1, 127.0, 108.2, 62.6, 61.9, 52.7, 48.8, 39.8, 31.1, 29.1, 16.2. HRMS: m/z 564.1845 [M+1]$^+$. $C_{22}H_{29}N_2O_3S_2$ (563.1773).

4-((4-(7-(4-cyano-2,6-dimethylphenoxy)thiazolo[4,5-d]pyrimidin-5-yl)amino)piperidin-1-yl)methyl)-N-cyclopropylbenzenesulfonamide (SZ3)

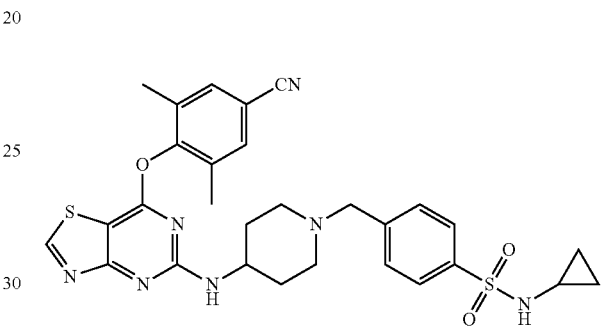

Starting with 9a and 4-(bromomethyl)-N-cyclopropylbenzenesulfonamide to afford SZ3 as a white solid. Yield: 55%, mp: 128-131° C.

$^1$H NMR (400 MHz, DMSO-$d_6$) δ 9.06 (s, 1H, thiazole-H), 8.95 (s, 1H, $SO_2NH$), 8.44 (d, J=7.5 Hz, 1H, NH), 7.78 (d, J=8.0 Hz, 2H, $C_3$, $C_5$-Ph'-H), 7.67 (s, 2H, $C_3$, $C_5$-Ph'-H), 7.53 (d, J=8.6 Hz, 2H, $C_2$, $C_6$-Ph'-H), 3.67-3.64 (m, 1H), 3.53 (s, 2H, N—$CH_2$), 2.80-2.78 (m, 2H), 2.27-2.26 (m, 1H), 2.10 (s, 6H), 1.92-1.52 (m, 4H), 1.42-1.29 (m, 2H), 0.47 (dd, J=7.0, 3.9 Hz, 2H), 0.38 (t, J=3.7 Hz, 2H). $^{13}$C NMR (100 MHz, DMSO-$d_6$) δ 161.1, 156.6, 154.5, 150.2, 144.0, 139.2, 133.0, 132.7, 130.4, 129.6, 128.2, 127.2, 119.2, 61.9, 52.7, 48.8, 31.5, 31.1, 29.1, 26.8, 24.5, 16.2, 5.6. HRMS: m/z 590.2008 [M+1]$^+$. $C_{29}H_{31}N_2O_3S_2$ (589.1930).

3,5-dimethyl-4-((5-O-(4-(morpholinosulfonyl)benzyl)piperidin-4-yl)amino)thiazolo[4,5-d]pyrimidin-7-yl)oxy)benzonitrile (SZ4)

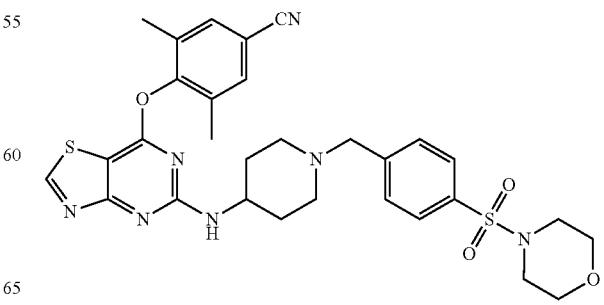

Starting with 9a and 4-((4-(bromomethyl)phenyl)sulfonyl)morpholine to afford SZ4 as a white solid. Yield: 57%, mp: 114-117° C.

$^1$H NMR (400 MHz, DMSO-d$_6$) δ 9.06 (s, 1H, thiazole-H), 8.44 (d, J=7.5 Hz, 1H, NH), 7.71 (d, J=9.3 Hz, 2H, C$_3$, C$_5$-Ph'-H), 7.67 (s, 2H, C$_3$, C$_5$-Ph'-H), 7.59 (d, J=8.3 Hz, 2H, C$_2$, C$_6$-Ph'-H), 3.67-3.64 (m, 1H), 3.63 (d, J=4.7 Hz, 4H), 3.56 (s, 2H, N—CH$_2$), 2.86 (d, J=4.8 Hz, 4H), 2.80-2.79 (m, 2H), 2.10 (s, 6H), 1.96-1.76 (m, 2H), 1.75-1.52 (m, 4H). $^{13}$C NMR (100 MHz, DMSO-d$_6$) δ 161.1, 154.5, 150.2, 145.1, 133.3, 133.0, 132.7, 129.8, 128.2, 128.2, 128.1, 108.2, 65.7, 61.8, 52.8, 48.8, 46.3, 39.6, 31.1, 16.2. HRMS: m/z 620.2111 [M+1]$^+$. C$_{30}$H$_{33}$N$_7$O$_4$S$_2$ (619.2035).

4-((4-(7-(4-cyano-2,6-dimethylphenoxy)thiazolo[4,5-d]pyrimidin-5-yl)amino)piperidin-1-yl)methyl)benzamide (SZ5)

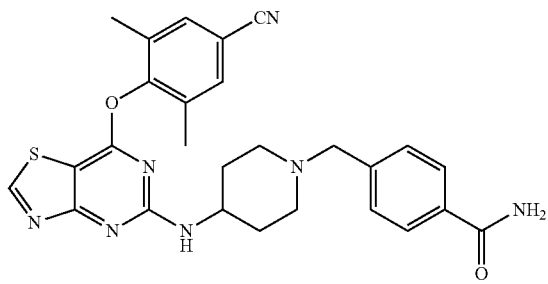 [SMILES: Cc1cc(C#N)cc(C)c1Oc1nc(NC2CCN(Cc3ccc(C(N)=O)cc3)CC2)nc2ncsc12]

Starting with 9a and 4-(chloromethyl)benzamide to afford SZ5 as a white solid. Yield: 51%, mp: 172-174° C.

$^1$H NMR (400 MHz, DMSO-d$_6$) δ 9.06 (s, 1H, thiazole-H), 8.43 (d, J=7.5 Hz, 1H, NH), 7.80 (d, J=7.8 Hz, 2H, C$_3$, C$_5$-Ph'-H), 7.67 (s, 2H, C$_3$, C$_5$-Ph'-H), 7.45 (d, J=8.0 Hz, 2H, C$_2$, C$_6$-Ph'-H), 7.31 (s, 2H, CONH$_2$), 3.68-3.64 (m, 1H), 3.48 (s, 2H, N—CH$_2$), 2.80-2.77 (m, 2H), 2.10 (s, 6H), 1.92-1.78 (m, 2H), 1.70-1.59 (m, 4H). $^{13}$C NMR (100 MHz, DMSO-d$_6$) δ 168.2, 161.0, 156.5, 154.7, 150.9, 142.2, 133.7, 133.1, 132.7, 129.0, 127.7, 119.2, 108.8, 62.2, 52.4, 48.9, 39.6, 39.3, 31.1, 16.2. HRMS: m/z 514.2020 [M+1]$^+$. C$_{22}$H$_{22}$N$_7$O$_2$S (513.1947).

3,5-dimethyl-4-((5-((1-(4-(methylsulfonyl)benzyl)piperidin-4-yl)amino)thiazolo[4,5-d]pyrimidin-7-yl)oxy)benzonitrile (SZ6)

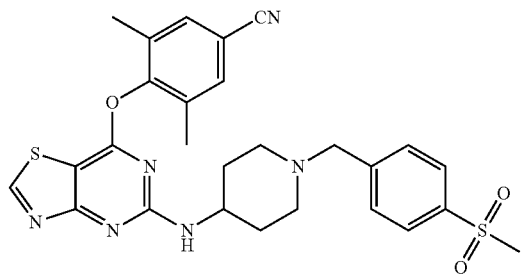 [SMILES: Cc1cc(C#N)cc(C)c1Oc1nc(NC2CCN(Cc3ccc(S(C)(=O)=O)cc3)CC2)nc2ncsc12]

Starting with 9a and 1-(bromomethyl)-4-(methylsulfonyl)benzene to afford SZ6 as a white solid. Yield: 76%, mp: 118-120° C.

$^1$H NMR (400 MHz, DMSO-d$_6$) δ 9.07 (s, 1H, thiazole-H), 8.44 (d, J=7.5 Hz, 1H, NH), 7.88 (d, J=8.1 Hz, 2H, C$_3$, C$_5$-Ph'-H), 7.67 (s, 2H, C$_3$, C$_5$-Ph'-H), 7.59 (d, J=8.1 Hz, 2H, C$_2$, C$_6$-Ph'-H), 3.65-3.63 (m, 1H), 3.55 (s, 2H, N—CH$_2$), 3.22 (s, 3H, SO$_2$CH$_3$), 2.78 (d, J=11.4 Hz, 2H), 2.10 (s, 6H), 1.99-1.83 (m, 3H), 1.77-1.60 (m, 3H). $^{13}$C NMR (100 MHz, DMSO-d$_6$) δ 163.3, 160.3, 154.4, 150.2, 145.4, 145.3, 139.8, 139.8, 139.5, 133.0, 132.7, 129.8, 127.4, 119.0, 108.9, 108.2, 62.6, 61.8, 52.7, 48.8, 44.1, 44.0, 39.4, 31.5, 31.1, 16.2. HRMS: m/z 549.1737 [M+1]$^+$. C$_{22}$H$_{28}$N$_6$O$_3$S$_2$ (548.1664).

3,5-dimethyl-4-((5-((1-(pyridin-4-ylmethyl)piperidin-4-yl)amino)thiazolo[4,5-d]pyrimidin-7-yl)oxy)benzonitrile (SZ7)

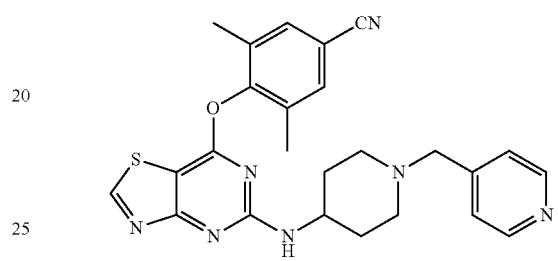

Starting with 9a and 4-(chloromethyl)pyridine to afford SZ7 as a white solid. Yield: 52%, mp: 118-120° C.

$^1$H NMR (400 MHz, DMSO-d$_6$) δ 9.07 (s, 1H, thiazole-H), 8.52 (d, J=5.9 Hz, 1H, NH), 8.46 (d, J=7.5 Hz, 2H, C$_3$, C$_5$-Ph'-H), 7.67 (s, 2H, C$_3$, C$_5$-Ph'-H), 7.32 (d, J=7.2 Hz, 2H, C$_2$, C$_6$-Ph'-H), 3.65 (dt, J=8.2, 5.6 Hz, 1H), 3.48 (s, 2H, N—CH$_2$), 2.78-2.76 (m, 2H), 2.10 (s, 6H), 1.86 (dd, J=11.8, 2.7 Hz, 2H), 1.72-1.55 (m, 4H). $^{13}$C NMR (100 MHz, DMSO-d$_6$) δ 163.3, 161.1, 160.3, 156.5, 154.4, 150.2, 150.0, 149.9, 148.0, 133.0, 132.7, 128.2, 124.1, 119.0, 108.2, 61.2, 52.7, 48.7, 39.4, 31.1, 26.8, 16.2. HRMS: m/z 472.1917 [M+1]$^+$. C$_{26}$H$_{26}$N$_2$OS (471.1841).

3,5-dimethyl-4-((5-((1-(4-nitrobenzyl)piperidin-4-yl)amino)thiazolo[4,5-d]pyrimidin-7-yl)oxy)benzonitrile (SZ8)

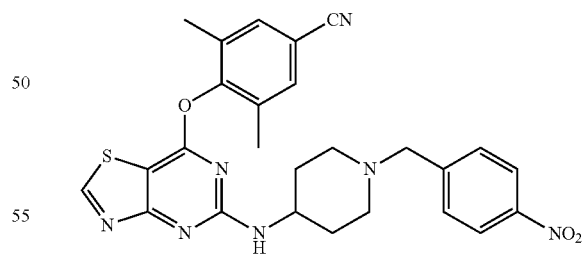

Starting with 9a and 1-(chloromethyl)-4-nitrobenzene to afford SZ8 as a white solid. Yield: 66%, mp: 145-147° C.

$^1$H NMR (400 MHz, DMSO-d$_6$) δ 9.06 (s, 1H, thiazole-H), 8.45 (d, J=7.6 Hz, 1H, NH), 8.21 (d, J=8.4 Hz, 2H, C$_3$, C$_5$-Ph'-H), 7.67 (s, 2H, C$_3$, C$_5$-Ph'-H), 7.59 (d, J=8.8 Hz, 2H, C$_2$, C$_6$-Ph'-H), 3.65-3.63 (m, 1H), 3.59 (s, 2H, N—CH$_2$), 2.78 (d, J=11.5 Hz, 2H), 2.09 (s, 6H), 1.89 (dd, J=12.7, 10.1 Hz, 2H), 1.78-1.50 (m, 4H). $^{13}$C NMR (101 MHz, DMSO-d$_6$) δ 163.3, 161.2, 156.6, 154.4, 150.4, 147.0, 133.0, 132.7, 130.1, 130.0, 123.8, 61.6, 52.7, 48.7, 39.8, 39.6, 39.4, 31.1, 16.2. ESI-MS: m/z 516.1814 [M+1]$^+$. C$_{26}$H$_{26}$N$_2$O$_3$S (515.1740).

3-((4-(7-(4-cyano-2,6-dimethylphenoxy)thiazolo[4,5-d]pyrimidin-5-yl)amino)piperidin-1-yl)methyl)benzamide (SZ9)

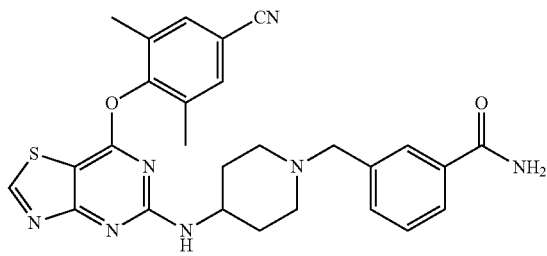 [SMILES: Cc1cc(C#N)cc(C)c1Oc1nc(NC2CCN(Cc3cccc(C(N)=O)c3)CC2)nc2ncsc12]

Starting with 9a and 3-(chloromethyl)benzamide to afford SZ9 as a white solid. Yield: 74%, mp: 153-155° C.

$^1$H NMR (400 MHz, DMSO-d$_6$) δ 8.95 (s, 1H, thiazole-H), 7.97 (s, 1H, NH), 7.78 (d, J=8.0 Hz, 2H, C$_3$, C$_5$-Ph'-H), 7.73 (s, 2H, C$_3$, C$_5$-Ph'-H), 7.45 (d, J=8.4 Hz, 2H, C$_2$, C$_6$-Ph'-H), 7.37 (s, 2H, CONH$_2$), 3.71 (s, 1H), 3.48 (s, 2H, N—CH$_2$), 2.84-2.65 (m, 2H), 2.12 (s, 6H), 2.03-1.75 (m, 3H), 1.63-1.26 (m, 3H). $^{13}$C NMR (100 MHz, DMSO-d$_6$) δ 168.4, 163.7, 161.1, 156.2, 154.4, 150.4, 139.9, 134.4, 133.0, 132.6, 132.1, 128.7, 128.2, 126.0, 119.2, 108.4, 62.4, 52.3, 48.8, 31.7, 16.2. HRMS: m/z 514.2022 [M+1]$^+$. C$_{22}$H$_{22}$N$_2$O$_2$S (513.1947).

4-((4-(7-(4-cyano-2,6-dimethylphenoxy)thiazolo[5,4-d]pyrimidin-5-yl)amino)piperidin-1-yl)methyl)benzenesulfonamide (TZ1)

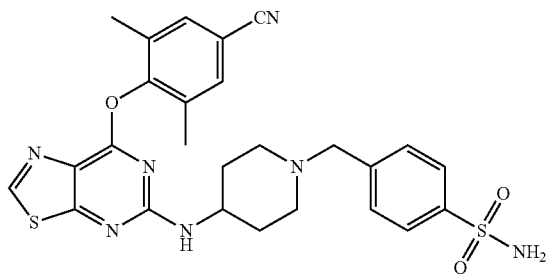 [SMILES: Cc1cc(C#N)cc(C)c1Oc1nc(NC2CCN(Cc3ccc(S(N)(=O)=O)cc3)CC2)nc2scnc12]

Starting with 9b and 4-(bromomethyl)benzenesulfonamide to afford TZ1 as a white solid. Yield: 66%, mp: 158-161° C.

$^1$H NMR (400 MHz, DMSO-d$_6$) δ 9.06 (s, 1H, thiazole-H), 8.44 (d, J=7.5 Hz, 1H, NH), 7.80 (d, J=8.0 Hz, 2H, C$_3$, C$_5$-Ph'-H), 7.67 (s, 2H, C$_3$, C$_5$-Ph'-H), 7.49 (d, J=8.3 Hz, 2H, C$_2$, C$_6$-Ph'-H), 7.33 (s, 2H, SO$_2$NH$_2$), 3.69-3.55 (m, 1H), 3.50 (s, 2H, N—CH$_2$), 2.82-2.70 (m, 2H), 2.09 (s, 6H), 1.88-1.85 (m, 3H), 1.73-1.54 (m, 3H). $^{13}$C NMR (100 MHz, DMSO-d$_6$) δ 156.5, 154.5, 150.2, 143.2, 143.2, 133.0, 132.7, 129.5, 126.1, 119.2, 108.2, 61.9, 52.7, 48.8, 39.4, 31.1, 16.2. HRMS: m/z 550.1691 [M+1]$^+$. C$_{26}$H$_{22}$N$_2$O$_3$S$_2$ (549.1617).

4-((4-(7-(4-cyano-2,6-dimethylphenoxy)thiazolo[5,4-d]pyrimidin-5-yl)amino)piperidin-1-yl)methyl)benzamide (TZ2)

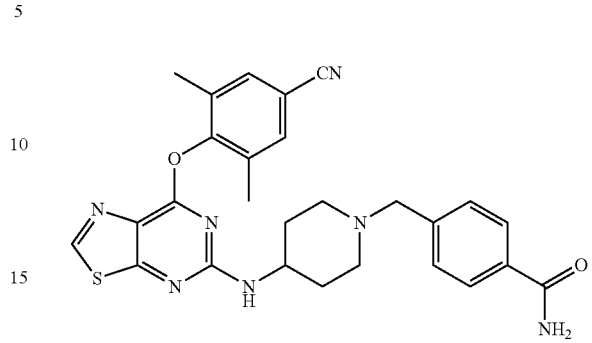

Starting with 9b and 4-(chloromethyl)benzamide to afford TZ2 as a white solid. Yield: 51%, mp: 144-146° C.

$^1$H NMR (400 MHz, DMSO-d$_6$) δ 9.06 (s, 1H, thiazole-H), 8.43 (d, J=7.5 Hz, 1H, NH), 7.84 (d, J=7.9 Hz, 2H, C$_3$, C$_5$-Ph'-H), 7.67 (s, 2H, C$_3$, C$_5$-Ph'-H), 7.37 (d, J=8.1 Hz, 2H, C$_2$, C$_6$-Ph'-H), 7.32 (s, 2H, CONH$_2$), 3.70-3.57 (m, 1H), 3.48 (s, 2H, N—CH$_2$), 2.79-2.77 (m, 2H), 2.10 (s, 6H), 1.90-1.80 (m, 2H), 1.75-1.55 (m, 4H). $^{13}$C NMR (100 MHz, DMSO-d$_6$) δ 168.2, 161.1, 156.5, 154.5, 150.2, 142.4, 133.4, 133.0, 132.7, 128.9, 127.9, 119.2, 108.2, 62.2, 52.7, 48.9, 39.6, 39.4, 31.1, 16.2. HRMS: m/z 514.2019 [M+1]$^+$. C$_{22}$H$_{22}$N$_2$O$_2$S (513.1947).

3,5-dimethyl-4-((5-((1-(4-(methylsulfonyl)benzyl)piperidin-4-yl)amino)thiazolo[5,4-d]pyrimidin-7-yl)oxy)benzonitrile (TZ3)

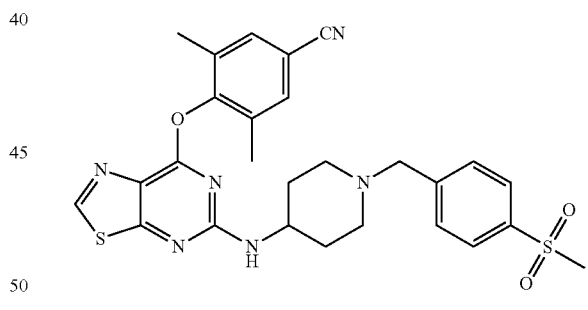

Starting with 9b and 1-(bromomethyl)-4-(methylsulfonyl)benzene to afford TZ3 as a white solid. Yield: 59%, mp: 112-114° C.

$^1$H NMR (400 MHz, DMSO-d$_6$) δ 9.06 (s, 1H, thiazole-H), 8.44 (d, J=7.5 Hz, 1H, NH), 7.90 (d, J=8.0 Hz, 2H, C$_3$, C$_5$-Ph'-H), 7.67 (s, 2H, C$_3$, C$_5$-Ph'-H), 7.58 (d, J=8.0 Hz, 2H, C$_2$, C$_6$-Ph'-H), 3.63-3.62 (m, 1H), 3.55 (s, 2H, N—CH$_2$), 3.22 (s, 3H, SO$_2$CH$_3$), 2.78 (d, J=11.3 Hz, 2H), 2.10 (s, 6H), 1.98-1.81 (m, 2H), 1.77-1.51 (m, 4H). $^{13}$C NMR (100 MHz, DMSO-d$_6$) δ 163.3, 161.1, 156.5, 154.4, 150.2, 145.3, 139.8, 133.0, 132.7, 129.8, 127.4, 127.2, 119.2, 108.2, 61.8, 52.7, 48.8, 44.0, 39.8, 39.4, 31.1, 16.2. HRMS: m/z 549.1714 [M+1]$^+$. C$_{22}$H$_{28}$N$_6$O$_3$S$_2$ (548.1664).

3,5-dimethyl-4-((5-((1-(pyridin-4-ylmethyl)piperidin-4-yl)amino)thiazolo[5,4-d]pyrimidin-7-yl)oxy)benzonitrile (TZ4)

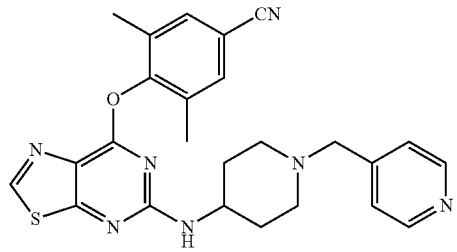 [SMILES: Cc1cc(C#N)cc(C)c1Oc1nc(NC2CCN(Cc3ccncc3)CC2)nc2scnc12]

Starting with 9b and 4-(chloromethyl)pyridine to afford TZ4 as a white solid. Yield: 44%, mp: 116-118° C.

$^1$H NMR (400 MHz, DMSO-$d_6$) δ 9.07 (s, 1H, thiazole-H), 8.52 (d, J=5.5 Hz, 1H, NH), 8.44 (d, J=7.5 Hz, 2H, $C_3$, $C_5$-Ph'-H), 7.67 (s, 2H, $C_3$, $C_5$-Ph'-H), 7.34-7.29 (m, 2H, $C_2$, $C_6$-Ph'-H), 3.66-3.63 (m, 1H), 3.48 (s, 2H, N—$CH_2$), 2.78-2.76 (m, 2H), 2.10 (s, 6H), 1.90-1.84 (m, 3H), 1.74-1.36 (m, 3H). $^{13}$C NMR (100 MHz, DMSO-$d_6$) δ 163.3, 156.6, 154.4, 150.2, 150.0, 149.9, 148.0, 133.0, 132.7, 128.2, 124.1, 119.2, 108.2, 61.2, 52.7, 48.7, 39.6, 31.1, 16.2. HRMS: m/z 472.1918 [M+1]$^+$. $C_{26}H_{26}N_7OS$ (471.1841).

3,5-dimethyl-4-((5-((1-(4-nitrobenzyl)piperidin-4-yl)amino)thiazolo[5,4-d]pyrimidin-7-yl)oxy)benzonitrile (TZ5)

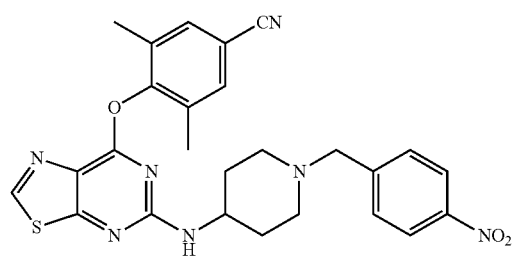

Starting with 9b and 1-(chloromethyl)-4-nitrobenzene to afford TZ5 as a white solid. Yield: 51%, mp: 146-148° C.

$^1$H NMR (400 MHz, DMSO-$d_6$) δ 9.07 (s, 1H, thiazole-H), 8.45 (d, J=7.5 Hz, 1H, NH), 8.22 (d, J=8.4 Hz, 2H, $C_3$, $C_5$-Ph'-H), 7.67 (s, 2H, $C_3$, $C_5$-Ph'-H), 7.59 (d, J=8.5 Hz, 2H, $C_2$, $C_6$-Ph'-H), 3.65 (dt, J=8.0, 5.2 Hz, 1H), 3.59 (s, 2H, N—$CH_2$), 2.78 (d, J=11.3 Hz, 2H), 2.10 (s, 6H), 1.89 (dt, J=11.6, 6.0 Hz, 2H), 1.78-1.55 (m, 4H). $^{13}$C NMR (100 MHz, DMSO-$d_6$) δ 163.3, 161.1, 156.6, 154.4, 150.3, 147.4, 147.0, 133.0, 132.7, 130.1, 128.2, 123.8, 119.2, 108.2, 61.6, 52.7, 48.7, 31.1, 16.2. HRMS: m/z 516.1817 [M+1]$^+$. $C_{26}H_{26}N_7O_3S$ (515.1740).

3-((4-(7-(4-cyano-2,6-dimethylphenoxy)thiazolo[5,4-d]pyrimidin-5-yl)amino)piperidin-1-yl)methyl)benzamide (TZ6)

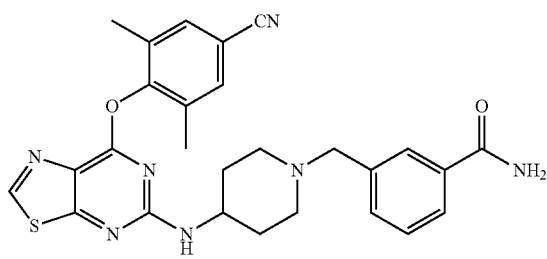 [SMILES: Cc1cc(C#N)cc(C)c1Oc1nc(NC2CCN(Cc3cccc(C(N)=O)c3)CC2)nc2scnc12]

Starting with 9b and 3-(chloromethyl)benzamide to afford TZ6 as a white solid. Yield: 73%, mp: 154-156° C.

$^1$H NMR (400 MHz, DMSO-$d_6$) δ 9.06 (s, 1H, thiazole-H), 8.44 (d, J=7.6 Hz, 1H, NH), 7.80 (d, J=8.4 Hz, 2H, $C_3$, $C_5$-Ph'-H), 7.67 (s, 2H, $C_3$, $C_5$-Ph'-H), 7.47-7.40 (m, 2H, $C_2$, $C_6$-Ph'-H), 7.37 (s, 2H, $CONH_2$), 3.76-3.57 (m, 1H), 3.48 (s, 2H, N—$CH_2$), 2.79-2.77 (m, 2H), 2.10 (s, 6H), 1.90-1.86 (m, 2H), 1.75-1.53 (m, 4H). $^{13}$C NMR (100 MHz, DMSO-$d_6$) δ 168.4, 163.3, 161.1, 156.6, 154.4, 150.1, 139.1, 134.7, 133.0, 132.7, 132.1, 128.5, 128.2, 126.5, 119.2, 108.2, 62.4, 52.7, 48.8, 31.1, 16.2. HRMS: m/z 514.2020 [M+1]$^+$. $C_{22}H_{22}N_7O_2S$ (513.1947).

Example 6. In Vitro Anti-HIV Activity of the Target Compounds

Selected compounds were screened for inhibitory activity against HIV-1 using MTT method as describe previously by Christophe. Pannecouque et al. *Nat. Protoc.* 3 (2008) 427-434, and Rudi Pauwels et al. *J. Virol. Methods* 20(1988) 309-321. And in vitro anti-HIV activity of compounds were supported by Rega Institute for Medical Research. The MTT assay is based on the reduction of the yellow colored 3-(4,5-dimethylthiazol-2-yl)-2,5-diphenyltetrazolium bromide (MTT) by mitochondrial dehydrogenases of metabolically active cells to a blue formazan which can be measured spectrophotometrically. Tested optical density served as an indicator for live cells, and survival rate can be concluded by testing the optical density of 540 nm and 690 nm. MT-4 cells infected with HIV-1 can only survive for 5 to 7 days without any treatment, but when HIV-1 inhibitors were added, they can protect MT-4 cell from cytopathic. Serial solution of compounds was added to MT-4 cells after infected with HIV-1, MTT method was used to detect the survival rate after culture for 5 to 7 days. $EC_{50}$ value was defined as compound concentration required to achieve 50% protection of MT-4 cells against HIV-1-induced cytopathic effect.

Materials (1) MT-4 cells infected with HIV-1 viral strains (IIIB, K103N, Y181C, Y188L, Y181C/K103N) were provided by Rega Institute for Medical Research, Katholieke Universiteit Leuven, Belgium.

(2) MTT and formazan: sigma Chemical Co.

(3) Preparation of compounds: Stock solutions (10× final concentration) of test compounds is diluted with double distilled $H_2O$ for 5 folds and 5 concentrations of one compound are prepared.

(4) Reference drugs: Nevirapine (NVP) and Etravirine (ETR).

(5) Test method (MTT method): Serial five-fold dilutions of test compounds were added to cultured MT-4 cells infected with HIV-1, after 5 to 7 days, MTT was added and cultured for a few hours. Medium was removed and lysate was added followed by formazan, OD value was determined in 690 nm and 540 nm by microplate reader, and $EC_{50}$ value was calculated.

Methods

The MTT method was described briefly as follows: stock solutions (10× final concentration) of test compounds were added in 25 μL volumes to two series of triplicate wells in order to allow simultaneous evaluation of the effects on mock- and HIV-infected cells. Using a Biomek 3000 robot (Beckman Instruments, Fullerton, Calif.), serial five-fold dilutions of the test compounds (final 200 μL volume per well) were made directly in flat-bottomed 96-well microtiter trays, including untreated control HIV-1 and mock-infected cell samples for each sample. HIV-1 (IIIB) and mutant HIV-1 strains stock (50 μL at 100-300 $CCID_{50}$) or culture medium was added to either the infected or mock-infected wells of the microtiter tray. Mock-infected cells were used to evaluate the effect of test compounds on uninfected cells to assess cytotoxicity. Exponentially growing MT-4 cells were centrifuged for 5 min at 1000 rpm and the supernatant was discarded. The MT-4 cells were resuspended at 6×105 cells/mL, and 50 μL aliquots were transferred to the microtiter tray wells. At five days after infection, the viability of mock- and HIV-infected cells was determined spectrophotometrically by means of MTT assay.

The MTT assay is based on the reduction of yellow-colored MTT (Acros Organics, Geel, Belgium) by mitochondrial dehydrogenase of metabolically active cells to form a blue-purple formazan that can be measured spectrophotometrically. The absorbances were read in an eight-channel computer-controlled photometer, at the wavelengths of 540 and 690 nm. All data were calculated using the median optical density (OD) value of three wells. The $EC_{50}$ was defined as the concentration of the test compound affording 50% protection from viral cytopathogenicity. The $CC_{50}$ was defined as the compound concentration that reduced the absorbance ($OD_{540}$) of mock-infected cells by 50%. The results are shown in Tables 1-2.

TABLE 1

The activity, cytotoxicity and SI values of some representative compounds

| | [a]$EC_{50}$ (nM) | | [b]$CC_{50}$ (μM) | [c]SI | |
|---|---|---|---|---|---|
| 编号 | IIIB | RES056 | | IIIB | RES056 |
| SZ1 | 2.2 ± 0.9 | 26.1 ± 1.5 | 25.1 ± 0.749 | 11071 | 961 |
| SZ2 | 4.8 ± 0.1 | 19.4 ± 13.1 | 13.7 ± 3.47 | 2828 | 710 |
| SZ3 | 5.0 ± 0.2 | 41.3 ± 5.2 | 23.2 ± 4.52 | 4564 | 561 |
| SZ4 | 3.7 ± 0.8 | 94.4 ± 0.5 | 17.6 ± 2.37 | 4665 | 187 |
| SZ5 | >15560 | >15560 | 15.5 ± 2.84 | <1 | <1 |
| SZ6 | 2.2 ± 0.6 | 27.4 ± 0.3 | 10.9 ± 2.75 | 4816 | 400 |
| SZ7 | 1.8 ± 0.4 | 24.7 ± 1.9 | 30.3 ± 0.760 | 16818 | 1227 |
| SZ8 | 3.4 ± 0.2 | 128.6 ± 4.5 | 5.17 ± 0.134 | 1482 | 40 |
| SZ9 | 1.3 | 558.9 ± 8.5 | 27.3 ± 0.965 | 20099 | 49 |
| TZ1 | 1.6 ± 0.2 | 18.3 ± 2.3 | 23.2 ± 1.75 | 14194 | 1265 |
| TZ2 | 1.6 ± 0.1 | 28.1 ± 13.0 | 27.1 ± 1.30 | 16412 | 965 |
| TZ3 | 2.3 ± 0.7 | 18.1 ± 1.1 | 14.3 ± 5.50 | 6212 | 791 |
| TZ4 | 2.7 | 26.8 ± 0.1 | 28.7 ± 0.489 | 10447 | 1074 |
| TZ5 | 8.2 ± 1.9 | 125.9 ± 16.0 | 5.68 ± 0.423 | 687 | 45 |
| TZ6 | 3.0 ± 0.6 | 222.3 ± 47.0 | 28.8 ± 0.634 | 9565 | 130 |
| NVP | 163 ± 41.2 | >9513 | >9.51 | >58 | X1 |
| ETR | 5.1 ± 0.8 | 45.4 ± 15.5 | >4.59 | >889 | >101 |

[a]$EC_{50}$: concentration of compound required to achieve 50% protection of MT-4 cell cultures against HIV-1-induced cytopathic, as determined by the MTT method.
[b]$CC_{50}$: concentration required to reduce the viability of mock-infected cell cultures by 50%, as determined by the MTT method.
[c]SI: selectivity index, the ratio of $CC_{50}/EC_{50}$.

TABLE 2

Activity against mutant HIV-1 strains

| | $EC_{50}$ (nM) | | | | | |
|---|---|---|---|---|---|---|
| 编号 | L100I | K103N | Y181C | Y188L | E138K | F227L + V106A |
| SZ1 | 7.8 ± 0.2 | 3.9 ± 1.9 | 6.7 ± 1.2 | 11.4 ± 2.3 | 6.5 ± 1.5 | 18.8 ± 4.5 |
| SZ2 | 8.7 ± 0.3 | 5.1 ± 1.0 | 7.3 ± 0.1 | 14.0 ± 2.0 | 9.2 ± 0.7 | 22.6 ± 3.8 |
| SZ6 | 3.2 ± 0.7 | 3.8 ± 2.8 | 7.0 ± 0.9 | 10.7 | 6.1 ± 1.1 | 15.4 ± 2.3 |
| SZ7 | 5.6 ± 2.2 | 1.9 ± 0.6 | 5.8 ± 2.2 | 7.7 ± 1.0 | 5.5 ± 1.2 | 32.9 ± 23.8 |
| TZ1 | 9.6 ± 1.5 | 1.9 ± 0.1 | 6.5 ± 1.0 | 10.8 ± 0.6 | 7.9 ± 0.1 | 16.0 ± 4.6 |
| TZ2 | 6.3 ± 2.8 | 1.6 ± 0.4 | 5.1 ± 0.1 | 7.2 ± 0.2 | 5.2 ± 0.8 | 20.3 ± 2.6 |
| TZ3 | 5.6 ± 0.7 | 3.3 ± 0.3 | 7.5 ± 0.6 | 7.1 ± 0.2 | 6.6 ± 0.1 | 15.2 ± 3.4 |
| TZ4 | 13.7 ± 7.1 | 3.3 ± 2.3 | 5.8 ± 0.1 | 6.6 ± 1.0 | 6.5 ± 0.3 | 30.9 ± 6.2 |
| ETR | 6.0 ± 1.5 | 3.3 ± 0.6 | 14.5 ± 8.2 | 20.4 ± 8.6 | 9.7 ± 6.9 | 19.7 ± 7.3 |

What is claimed is:
1. A compound of thiazolopyrimidine and its pharmaceutically acceptable salt, wherein the compound is selected from the group consisting of:
(SZ1)
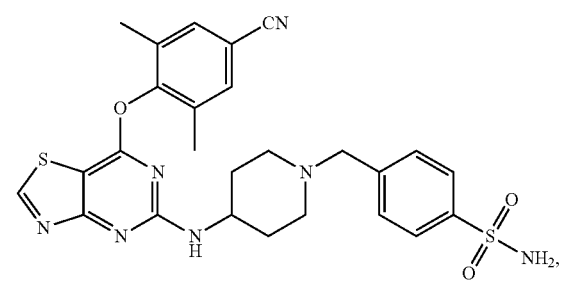
(SZ2)
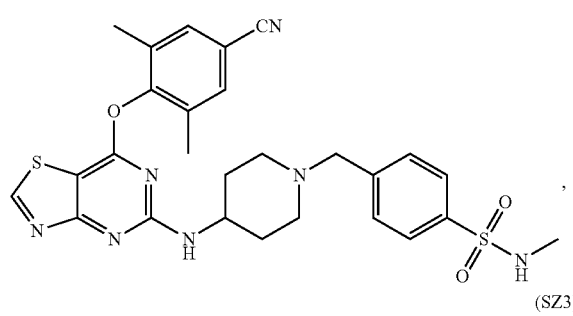
,
(SZ3)
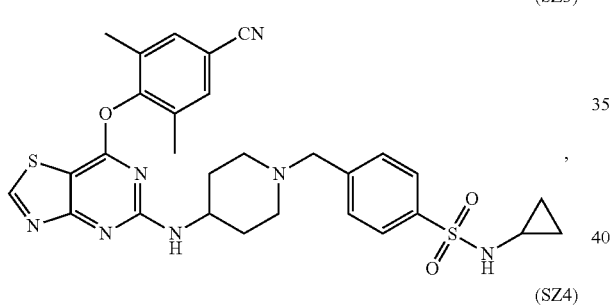
,
(SZ4)
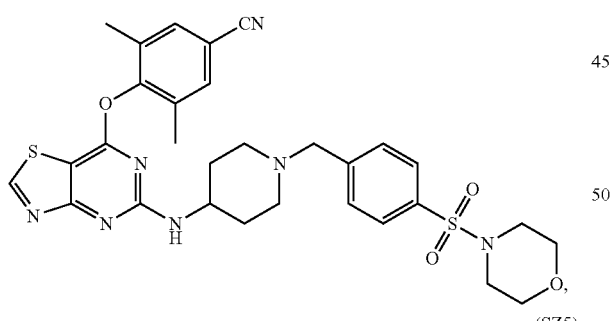
(SZ5)
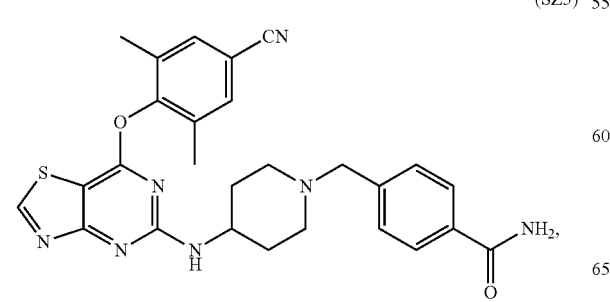
,
-continued
(SZ6)
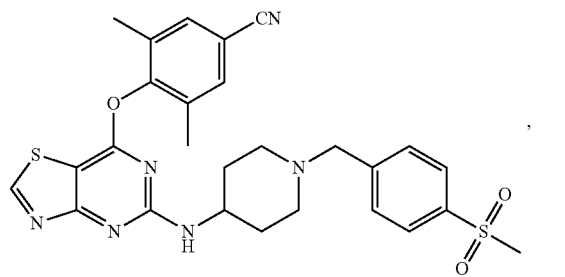
,
(SZ7)
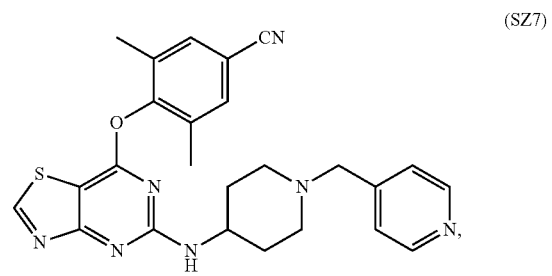
,
(SZ8)
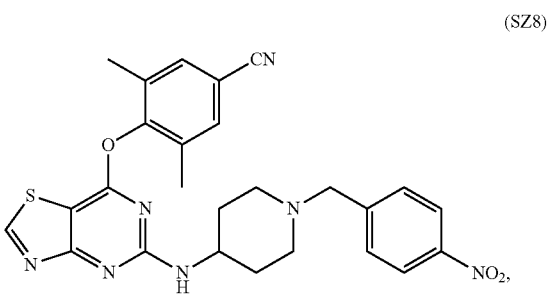
,
(SZ9)
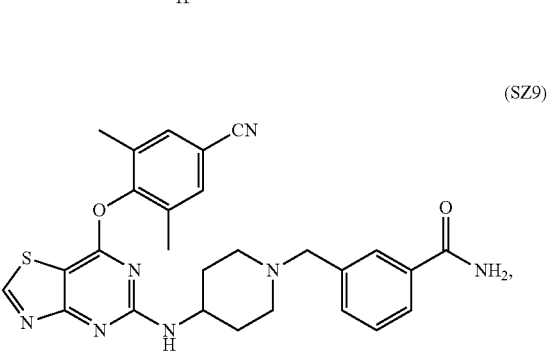
,
(SZ10)
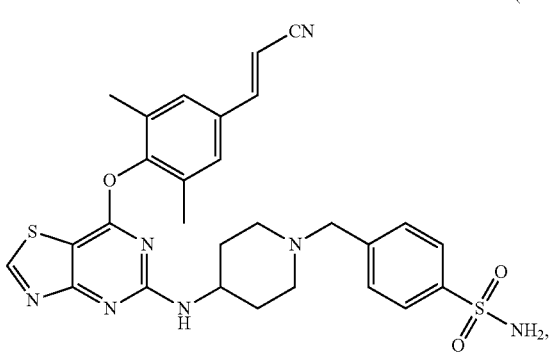
,

(TZ1)
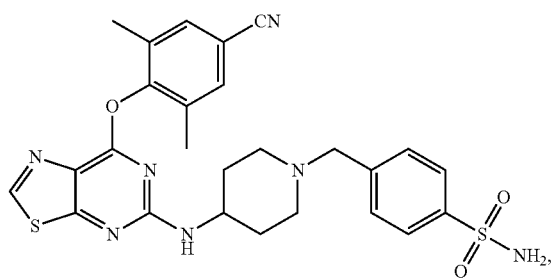

(TZ2)
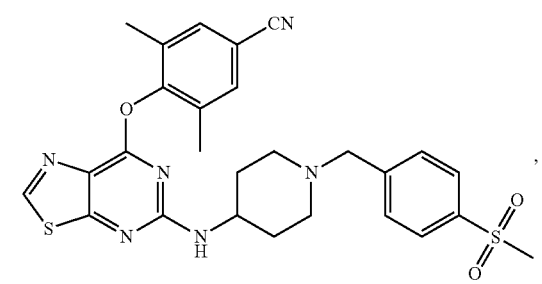

(TZ3)
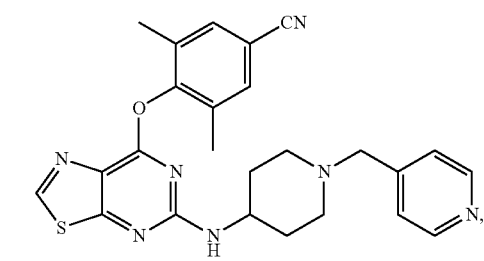

(TZ4)

(TZ5)
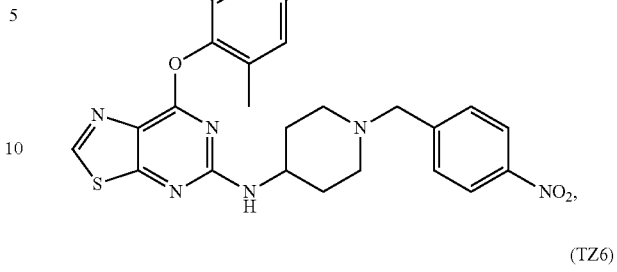

(TZ6)
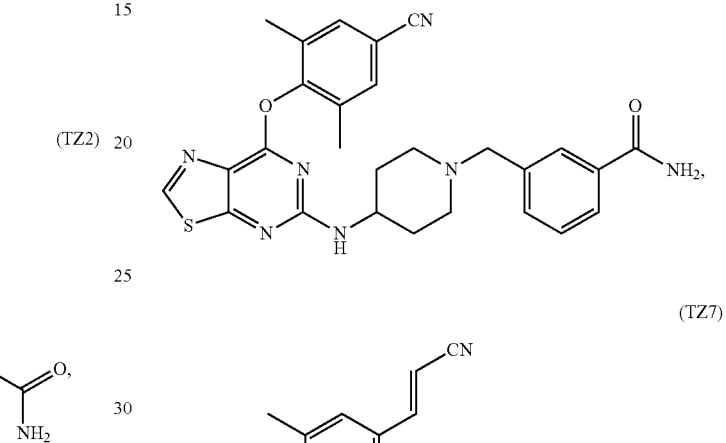

(TZ7)
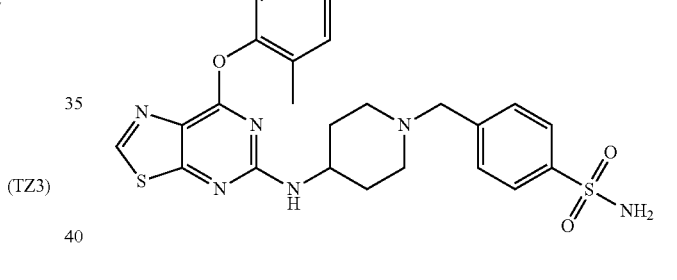

(TZ8)
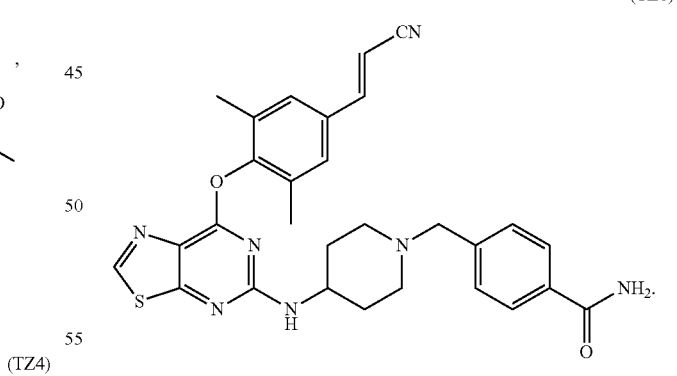

2. The compound according to claim 1, wherein the compound is prepared by the following steps:

reacting 2,4-dichloro-substituted thiazolopyrimidine 1a or 1b with substituted phenol or aniline via nucleophilic substitution reaction, yielding an intermediate 2a or 2b; treating the intermediate 2a or 2b with N-Boc-4-aminopiperidine, yielding intermediates 3a or 3b, respectively, which is deprotected with trifluoroacetic acid in dichloromethane, to yielding intermediate 4a or 4b, respectively; converting the intermediate 4a or 4b into the compound by nucleophilic substitution with various substitutes of benzyl chloride or benzyl bromide; wherein chemical reaction equations are as follows:

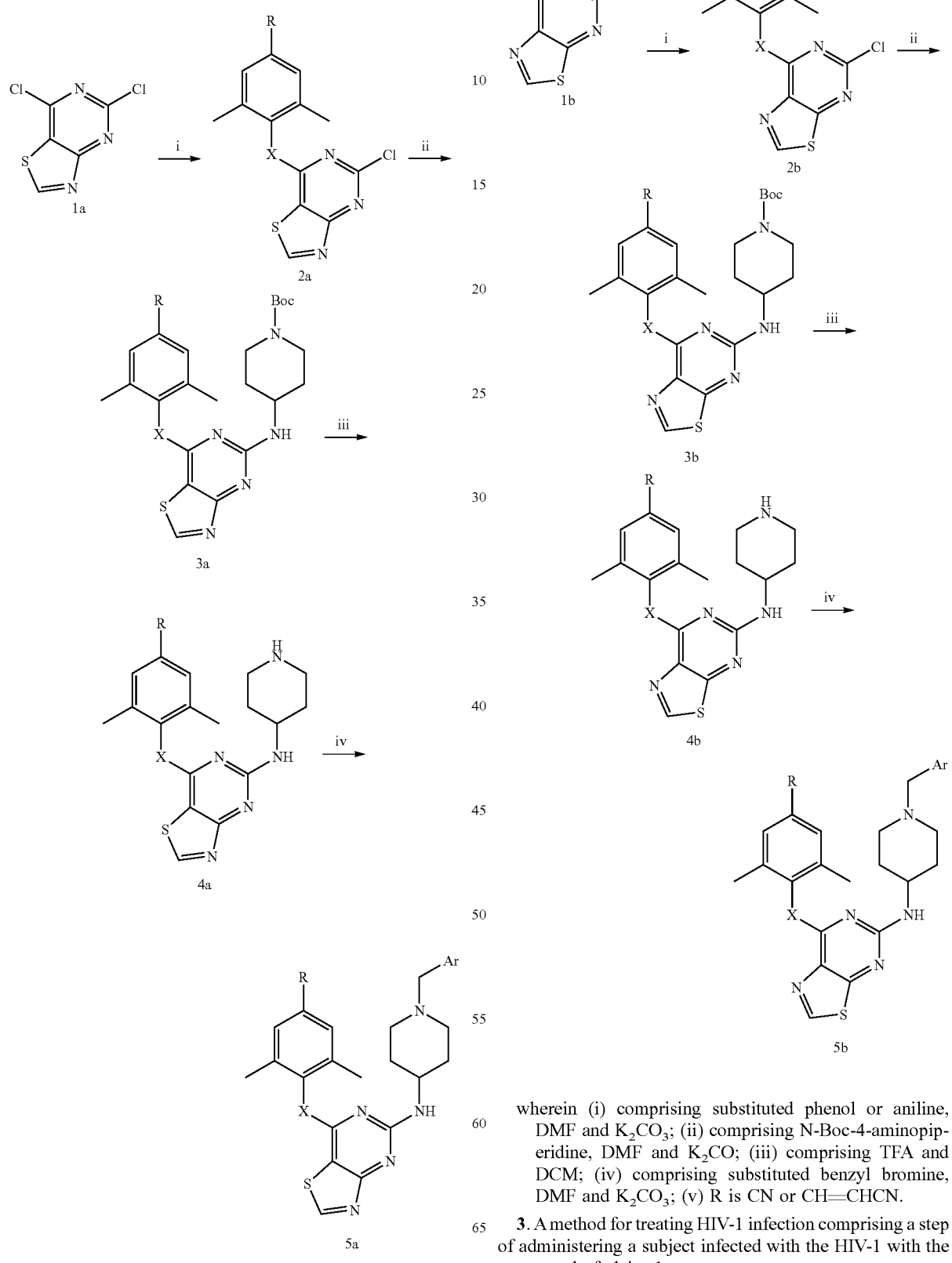

wherein (i) comprising substituted phenol or aniline, DMF and K$_2$CO$_3$; (ii) comprising N-Boc-4-aminopiperidine, DMF and K$_2$CO; (iii) comprising TFA and DCM; (iv) comprising substituted benzyl bromine, DMF and K$_2$CO$_3$; (v) R is CN or CH=CHCN.

3. A method for treating HIV-1 infection comprising a step of administering a subject infected with the HIV-1 with the compound of claim 1.

4. A pharmaceutical composition comprising the compound of claim 1, and one or more pharmaceutically acceptable carriers or excipients.

\* \* \* \* \*